(12) United States Patent
Tsou et al.

(10) Patent No.: US 8,247,224 B2
(45) Date of Patent: Aug. 21, 2012

(54) RECOMBINANT CONSTRUCT FOR DETECTION OF HALOGENATED AROMATIC HYDROCARBONS

(75) Inventors: Tsui-Chun Tsou, Zhunan (TW); Lih-Ann Li, Zhunan (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 12/726,099

(22) Filed: Mar. 17, 2010

(65) Prior Publication Data

US 2011/0229904 A1 Sep. 22, 2011

(51) Int. Cl.
*C12N 15/63* (2006.01)
*C12N 15/85* (2006.01)

(52) U.S. Cl. ..................... 435/320.1; 435/455

(58) Field of Classification Search ............... None
See application file for complete search history.

(56) References Cited

U.S. PATENT DOCUMENTS

| | | | |
|---|---|---|---|
| 5,854,010 A | 12/1998 | Denison | |
| 6,576,422 B1 | 6/2003 | Weinstein | |
| 6,720,431 B2 | 4/2004 | Chu | |

OTHER PUBLICATIONS

Yu et al (Cancer Research, vol. 59, pp. 1498-1504, 1999).*
Garrison, et al., "Species-Specific Recombinant Cell Lines as Bioassay Systems for the Detection of 2,3,7,8- Tetrachlorodibenzo-p-dioxin-like Chemicals", Fundamental and Applied Toxicology 30, 194-203 (1996) Article No. 0056.

* cited by examiner

*Primary Examiner* — Celine Qian
(74) *Attorney, Agent, or Firm* — Occhiuti Rohlicek & Tsao LLP

(57) ABSTRACT

The present invention describes a recombinant construct for detection of halogenated aromatic hydrocarbon compounds. A method for detecting halogenated aromatic hydrocarbon compounds using the recombinant construct is also described.

20 Claims, 9 Drawing Sheets

1. 5'DRE3,4 (SEQ ID NO: 4)
5'CGC GTC CCG GCC GGC G|CA CGC|AAG CTA GCA GCG CTT CT|C ACG|GA GCC GGG A3'
   Mlu I sticky end                                                    Bgl II sticky end 2. 3'DER3,4 (SEQ ID NO: 5)
5'GAT CTC CCG GCT C|GC GTG|AGA AGC GCT GCT AGC TT|G CGT G|CG CCG GCG A3'
   Bgl II sticky end                                                    Mlu I sticky end 3. 5'DRE5,6 (SEQ ID NO: 6)
5'CCC CTC |GCG TG|A CTG CGA GGT CCT TCT |CAC GG|A ACG CCT GA3'
   Kpn I sticky end                                      Mlu I sticky end 4. 3'DRE5,6 (SEQ ID NO: 7)
5'CGC GTC AGG CGT T|GC GTG|AGA AGG ACC TCG CAG T|CA CGC|GAG GGG GTA C3'
   Mlu I sticky end                                                    Kpn I sticky end

Fig. 2

```
TGCGATGAGTGGCAGGGCGGGGCGTAATTTTTTTAAGGCAGTTATTGGTGCCCTTAAACGCCTGGTTGC
TACGCCTGAATAAGTGATAATAAGCGGATGAATGGCAGAAATTCGCCGGATCTTTGTGAAGGAACCTTA
CTTCTGTGGTGTGACATAATTGGACAAACTACCTACAGAGATTTAAAGCTCTAAGGTAAATATAAAATT
TTTAAGTGTATAATGTGTTAAACTACTGATTCTAATTGTTTGTGTATTTTAGATTCCAACCTATGGAAC
TGATGAATGGGAGCAGTGGTGGAATGCCTTTAATGAGGAAAACCTGTTTTGCTCAGAAGAAATGCCATC
TAGTGATGATGAGGCTACTGCTGACTCTCAACATTCTACTCCTCCAAAAAAGAAGAGAAAGGTAGAAGA
CCCCAAGGACTTTCCTTCAGAATTGCTAAGTTTTTTGAGTCATGCTGTGTTTAGTAATAGAACTCTTGC
TTGCTTTGCTATTTACACCACAAAGGAAAAAGCTGCACTGCTATACAAGAAAATTATGGAAAAATATTC
TGTAACCTTTATAAGTAGGCATAACAGTTATAATCATAACATACTGTTTTTTCTTACTCCACACAGGCA
TAGAGTGTCTGCTATTAATAACTATGCTCAAAAATTGTGTACCTTTAGCTTTTTAATTTGTAAAGGGGT
TAATAAGGAATATTTGATGTATAGTGCCTTGACTAGAGATCATAATCAGCCATACCACATTTGTAGAGG
TTTTACTTGCTTTAAAAAACCTCCCACACCTCCCCCTGAACCTGAAACATAAAATGAATGCAATTGTTG
TTGTTAACTTGTTTATTGCAGCTTATAATGGTTACAAATAAAGCAATAGCATCACAAATTTCACAAATA
AAGCATTTTTTCACTGCATTCTAGTTGTGGTTTGTCCAAACTCATCAATGTATCTTATGATGTCTGGA
TCCGTCGACCGATGCCCTTGAGAGCCTTCAACCCAGTCAGCTCCTTCCGGTGGGCGCGGGGCATGACTA
    Sal I
```

CCCTCGCGTGACTGCGAGGTCCTTCTCACGCAACGCCTGACGCGTCGCCG
    DRE→                                 ←DRE

GCGCACGCAAGCTAGCAGCGCTTCTCACGCGAGCCGGG
    ←DRE                              ←DRE (C)

CCCGGGAGGTACCCCCTCGCGTGACTGCGAGGTCCTTCTCACGCAACGCCTGACGCGTCGCCGGCGCAC
       KpnI     DRE→                  ←DRE     MluI       ←DRE

GCAAGCTAGCAGCGCTTCTCACGCGAGCCGGGAGATCTAGAGGGTATATAATGGAATTCCTGCAGAAGC
              ←DRE       BglII      TATA          HindIII
                                     box
TT

CCCGGGAGGTACCCCTGGCGTGACTGCGAGGTCCTTCTCACGCAACGCCTGACGCGTCGCCGGCGCAC
CCAAGCTAGCAGCGCTTCTCACGCGAGCCGGGAGATCTAGAGGGTATATAATGGAATTCCTGCAGAAGC
TTGGCATTCCGGTACTGTTGGTAAAATGGAAGACGCCAAAAACATAAAGAAAGGCCCGGCGCCATTCTA
TCCTCTAGAGGATGGAACCGCTGGAGAGCAACTGCATAAGGCTATGAAGAGATACGCCCTGGTTCCTGG
AACAATTGCTTTTACAGATGCACATATCGAGGTGAACATCACGTACGCCGAATACTTCGAAATGTCCGT
TCGGTTGGCAGAAGCTATGAAACGATATGGGCTGAATACAAATCACAGAATCGTCGTATGCAGTGAAAA
CTCTCTTCAATTCTTTATGCCGGTGTTGGGCGCGTTATTTATCGGAGTTGCAGTTGCGCCCGCGAACGA
CATTTATAATGAACGTGAATTGCTCAACAGTATGAACATTTCGCAGCCTACCGTAGTGTTTGTTTCCAA
AAAGGGGTTGCAAAAAATTTTGAACGTGCAAAAAAAATTACCAATAATCCAGAAAATTATTATCATGGA
TTCTAAAACGGATTACCAGGGATTTCAGTCGATGTACACGTTCGTCACATCTCATCTACCTCCCGGTTT
TAATGAATACGATTTTGTACCAGAGTCCTTTGATCGTGACAAAACAATTGCACTGATAATGAATTCCTC
TGGATCTACTGGGTTACCTAAGGGTGTGGCCCTTCCGCATAGAACTGCCTGCGTCAGATTCTCGCATGC
CAGAGATCCTATTTTTGGCAATCAAATCATTCCGGATACTGCGATTTTAAGTGTTGTTCCATTCCATCA
CGGTTTTGGAATGTTTACTACACTCGGATATTTGATATGTGGATTTCGAGTCGTCTTAATGTATAGATT
TGAAGAAGCCTGTTTTTACGATCCCTTCAGGATTACAAAATTCAAAGTGCGTTGCTAGTACCAACCCT
ATTTTCATTCTTCGCCAAAAGCACTCTGATTGACAAATACGATTTATCTAATTTACACGAAATTGCTTC
TGGGGGCGCACCTCTTTCGAAAGAAGTCGGGGAAGCGGTTGCAAAACGCTTCCATCTTCCAGGGATACG
ACAAGGATATGGGCTCACTGAGACTACATCAGCTATTCTGATTACACCCGAGGGGGATGATAAACCGGG
CGCCGGTCGGTAAAGTTGTTCCATTTTTTGAAGCGAAGGTTGTGGATCTGGATACCGGGAAAACGCTGGG
CGTTAATCAGAGAGGCGAATTATGTGTCAGAGGACCTATGATTATGTCCGGTTATGTAAACAATCCGGA
AGCGACCAACGCCTTGATTGACAAGGATGGATGGCTACATTCTGGAGACATAGCTTACTGGGACGAAGA
CGAACACTTCTTCATAGTTGACCGCTTGAAGTCTTTAATTAAATACAAAGGATATCAGGTGGCCCCCGC
TGAATTGGAATCGATATTGTTACAACACCCCAACATCTTCGACGCGGGCGTGGCAGGTCTTCCCGACGA
TGACGCCGGTGAACTTCCCGCCGCCGTTGTTGTTTTGGAGCACGGAAAGACGATGACGGAAAAAGAGAT
CGTGGATTACGTCGCCAGTCAAGTAACAACCGCGAAAAAGTTGCGCGGAGGAGTTGTGTTTGTGGACGA
AGTACCGAAAGGTCTTACCGGAAAACTCGACGCAAGAAAAATCAGAGAGATCCTCATAAAGGCCAAGAA
GGGCGGAAAGTCCAAATTGTAAAATGTAACTGTATTCAGCGATGACGAAATTCTTAGCTATTGTAATAC

RECOMBINANT CONSTRUCT FOR DETECTION OF HALOGENATED AROMATIC HYDROCARBONS

FIELD OF THE INVENTION

The preset invention relates to a recombinant construct for detection of halogenated aromatic hydrocarbons (HAHs), and methods of using the same.

BACKGROUND OF THE INVENTION

Halogenated aromatic hydrocarbons (HAHs) are a diverse group of widespread anthropogenic environmental contaminants (*Chemosphere* 37, 1731-1741). These organochlorines compounds have been found widespread in ambient air (*Environ Sci Technol* 38, 4937-4944), stack flue gas (*Chemosphere* 50, 1123-1129), sediment (*Chemosphere* 31, 2863-2872), fish (*Environ Pollut* 141, 381-386), blood and placentas (*Chemosphere* 54, 1459-1473) as well as breast milk (*Food Chem Toxicol* 42, 1299-1308; *J Hazard Mater* 121, 1-10), and tend to bioaccumulate in the food chain. Some HAHs are highly toxic, and most of these compounds, such as polychlorinated dibenzo-p-dioxins (PCDDs), polychlorinated dibenzofurans (PCDFs) and polychlorinated biphenyls (PCBs), cause toxicity by binding to and activating the aryl hydrocarbon receptor (Ah receptor or AhR), in which 2,3,7,8-tetrachlorodibenzo-p-dioxin (2,3,7,8-TCDD) is the most extensively studied one and has therefore become a prototype for this class of toxic environmental contaminants.

One of the recent techniques for detection and quantification of these toxic compounds is high-resolution gas chromatography/high-resolution mass spectrometry (HRGC/HRMS), which is costly and time-consuming. As an alternative, the chemical activated luciferase expression (CALUX) bioassay is an in vitro luciferase-reporter-gene assay for detecting the Toxic Equivalents (TEQ) levels of these toxic compounds based on their ability to bind and activate AhR. U.S. Pat. No. 5,854,010 describes a recombinant cell line, the mouse H1L1.1 cell line, made by using generic engineering techniques for inserting dioxin responsive elements (DREs) upstream of a luciferase report gene and then transfecting the resultant recombinant expression plasmid into mouse hepatoma cells. Garrison et al. describes species-specific recombinant cell lines as bioassay systems for the detection of TCDD-like chemicals (*Fundam Appl Toxicol* 30, 194-203). However, these conventional bioassays rely on selection of stable responsive cell lines which can maintain their responsiveness to the toxic compounds for an expended period; however, most of the stable cell lines would gradually lose such responsiveness during cell passages.

BRIEF SUMMARY OF THE INVENTION

In this invention, we have designed a recombinant construct for detection of a HAH compound, which carries a reporter gene under the control of a regulatory sequence comprising a nucleotide sequence of SEQ ID NO: 1 and a promoter. The recombinant construct of the invention can be used in a bioassay for detecting a HAH compound. In comparison with the conventional bioassay for detecting a HAH compound using stable cell lines, the recombinant construct of the invention does not require stringent storage condition, such as liquid nitrogen, and can freshly infect host cells when needed without decay in the responsiveness to the toxic compounds due to cell passages.

Therefore, in one aspect, the present invention provides a recombinant construct for detection of a halogenated aromatic hydrocarbon (HAH) compound, comprising a reporter gene which is operatively linked to a regulatory sequence comprising a nucleotide sequence of SEQ ID NO: 1 and a promoter.

In particular, the recombinant construct of the invention is derived from an adenovirus, particularly a serotype 5 adenovirus (Ad5).

In another aspect, the present invention provides a method for determining if a halogenated aromatic hydrocarbon (HAH) compound is present in a sample comprising:
(a) introducing a recombinant construct of the invention into a host cell which expresses AhR;
(b) incubating the host cell with the sample; and
(c) detecting the expression of the reporter gene as indicator for the presence of the HAH compound in the sample.

Particularly, the HAH compound is capable of binding to the AhR. More particularly, the HAH compound is selected from the group consisting of polychlorinated dibenzo-p-dioxins (PCDDs), polychlorinated dibenzofurans (PCDFs), polychlorinated biphenyls (PCBs) and combinations thereof.

The various embodiments of the present invention are described in details below. Other characteristics of the present invention will be clearly presented by the following detailed descriptions and drawings about the various embodiments and claims.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown.

In the drawings:

FIG. 2 shows the nucleotide sequences of the four single-stranded DNA molecules of SEQ ID NOS: 4 to 7 as described in Example 1 wherein the framed segments indicate DREs.

DETAILED DESCRIPTION OF THE INVENTION

Figure 1:
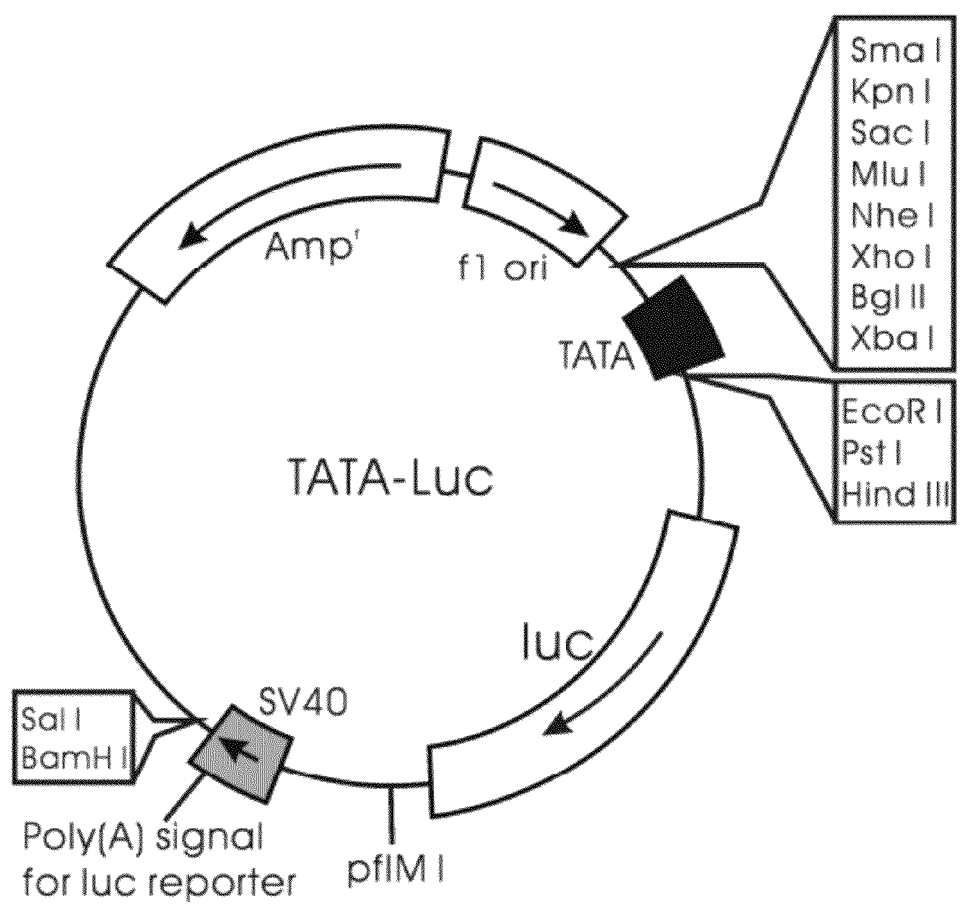
FIG. 1 shows the map of the TATA Luc vector as described in Example 1.

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to reference to "a sample" includes a plurality of such samples and equivalents thereof known to those skilled in the art.

The term "construct" or "vector" as used herein, refers to a nucleic acid molecule, such as a plasmid or virus, which contains one or more recombinant nucleotide sequences and can be used for expressing a given nucleotide sequence that has been cloned therein or mediate transfer of such nucleotide sequence between different host cells. As used herein, "nucleic acid" or "polynucleotide" refers to a polymer composed of nucleotide units, including naturally occurring nucleic acids, such as deoxyribonucleic acid ("DNA") and ribonucleic acid ("RNA") as well as nucleic acid analogs including those which have non-naturally occurring nucleotides, which include, but are not limited to, single-, double-, or multi-stranded DNA or RNA, genomic DNA, cDNA, mRNA, DNA-RNA hybrids, or a polymer comprising purine and pyrimidine bases or other natural, chemically or biochemically modified, non-natural, or derivatized nucleotide bases. It will be understood that when a nucleic acid fragment is represented by a DNA sequence (i.e., A, T, G, C), this also includes an RNA sequence (i.e., A, U, G, C) in which "U" replaces "T." A "viral construct" or "viral vector", e.g., an "adenoviral construct" or "adenoviral vector" is a polynucleotide construct or vector derived from a virus e.g. an adenovirus.

The term "recombinant" is used to describe a polynucleotide or nucleic acid having sequences that are not naturally joined together.

The term "operatively linked" as used herein with respect to a recombinant construct or vector means the nucleotide sequences of the recombinant construct or vector are functionally related to one another for operative control of a given coding sequence.

In one aspect, the present invention provides a recombinant construct for detection of a HAH compound, comprising a reporter gene which is operatively linked to a regulatory sequence comprising a nucleotide sequence of SEQ ID NO: 1 and a promoter.

In particular, the recombinant construct of the invention may be derived from an adenovirus, including any adenovirus of the 42 different serotypes or subgroups A-F as known in the art, such as a serotype 5 adenovirus (Ad5). Preferably, the adenovirus for use in the invention is replication defective e.g. lacking an adenovirus E1 region and/or E3 region. Certain commercially available replication-defective adenovirus products such as pAdEasy-1 (Stratagene, Calif.) or pJM17 (*Virology* 163, 614-617) may be used in the present invention. Generation and propagation of such replication defective adenovirus depend on helper cells such as 293 that complement the defects.

As used herein, a "reporter gene" refers to a polynucleotide that encodes a reporter (e.g. a polypeptide or protein) that can be specifically detected when expressed, for example, via its color or enzyme activity. Reporter genes are useful for determining the activation of the regulatory sequences responsible for expression of the reporter genes. Reporter genes suitable for use herein are conventional in this art, selection of which is within the capability of one skilled in the art. Examples of reporter genes include but are not limited to that encoding a bioluminescent reporter protein such as luciferase and that encoding a fluorescent reporter protein such as green fluorescent protein (GFP), cyan fluorescent protein (CFP), red fluorescent protein (RFP) or yellow fluorescent protein (YFP). Particularly, the reporter gene as used in the invention encodes a bioluminescent reporter protein. In one example of the invention, the reporter protein encodes luciferase.

As used herein, a "regulatory sequence" refers to a nucleic acid sequence containing one or more elements that are capable of affecting or effecting expression of a gene sequence, including transcription or translation thereof, when the gene sequence is placed in such a position as to subject it to the control thereof. Such a regulatory sequence may comprise, for example, a promoter sequence, an enhancer sequence, an upstream responsive sequence, an operator sequence, a downstream termination sequence, a polyadenylation sequence, an optimal 5' leader sequence to optimize initiation of translation, and a Shine-Dalgarno sequence.

As used herein a "promoter" usually contains specific DNA sequences (responsive elements) which provide binding sites for RNA polymerase and transcriptional factors for transcription to take place. Typically, a promoter is located near the genes it regulates on the same strand and upstream (towards the 5' region of the sense strand). Examples of promoters include the TATA box, the SV40 late promoter from simian virus 40, the SV40 late promoter from simian virus 40 and the T7 promoter. These promoter sequences are well known in the art. In one example of the invention, the promoter is a TATA box.

According to the invention, the reporter gene is operatively linked to a regulatory sequence comprising a promoter and a nucleotide sequence of SEQ ID NO: 1 such that the reporter gene is expressed under the control of the regulatory sequence. In one embodiment of the invention, the reporter gene is located downstream of the regulatory sequence in which the nucleotide sequences of SEQ ID NO: 1 is placed upstream of the promoter.

In a certain example of the invention, the recombinant nucleic acid construct comprises the nucleotide sequence of SEQ ID NO: 2.

In another example of the invention, the recombinant nucleic acid construct comprises the nucleotide sequence of SEQ ID NO: 3.

It is understood that any genetic engineering techniques may be used to prepare the recombinant construct of the invention such as polynucleotide synthesis, polymerase chain reaction (PCR), cloning, nucleic acid purification, vector construction, enzymatic treatment and sequencing of vectors and nucleic acid fragments, and cell transformation and transfection; see for example Sambrook et al., Molecular Cloning: A Laboratory Manual, $2^{nd}$ ed., Cold Spring Harbor Laboratory Press (1989), and Frederick M. A. et al., Current Protocols in Molecular Biology, John Wiley & Sons, Inc. (2001). Details for the preparation of the recombinant construct of the invention are described in the examples below.

As known in the art, the action of the HAH compounds is mediated through a cytosolic transcription factor, called the aryl hydrocarbon receptor (AhR). After binding of the ligand (HAH compounds), the resulted AhR complex binds to specific DNA sequences i.e. DREs, and then results in transcriptional activation of the adjacent responsive genes. The consensus sequence of the DREs is 5'-TNGCGTG-3' where N means any nucleotide of A, T, G and C.

Accordingly, in another aspect, the present invention provides a method for determining if a halogenated aromatic hydrocarbon (HAH) compound is present in a sample, comprising:

(a) introducing a recombinant construct as described above into a host cell that expresses AhR;
(b) incubating the host cell with the sample; and
(c) detecting the expression of the reporter gene as indicator for the presence of the HAH compound in the sample.

Particularly, the HAH compound is capable of binding to the AhR. More particularly, the HAH compound is selected from the group consisting of polychlorinated dibenzo-p-dioxins (PCDDs), polychlorinated dibenzofurans (PCDFs), polychlorinated biphenyls (PCBs) and combinations thereof. Certain examples of the HAH compound include 2,3,7,8-TCDD (tetrachlorodibenzo-p-dioxin), 1,2,3,7,8-PCDD (pentachlorodibenzo-p-dioxin), 1,2,3,4,7,8-HxCDD (hexachlorodibenzo-p-dioxin), 1,2,3,6,7,8-HxCDD (hexachlorodibenzo-p-dioxin), 1,2,3,7,8,9-HxCDD (hexachlorodibenzo-p-dioxin), 1,2,3,4,6,7,8-HpCDD (heptachlorodibenzo-p-dioxin), OCDD (octachlorodibenzo-p-dioxin), 2,3,7,8-TCDF (tetrachlorodibenzofuran), 1,2,3,7,8-PCDF (pentachlorodibenzofuran), 2,3,4,7,8-PCDF (pentachlorodibenzofuran), 1,2,3,4,7,8-HxCDF (hexachlorodibenzofuran), 1,2,3,6,7,8-HxCDF (hexachlorodibenzofuran), 1,2,3,7,8,9-HxCDF (hexachlorodibenzofuran), 2,3,4,6,7,8-HxCDF (hexachlorodibenzofuran), 1,2,3,4,6,7,8-HpCDF (heptachlorodibenzofuran), 1,2,3,4,7,8,9-HpCDF (heptachlorodibenzofuran), and OCDD (octachlorodibenzofuran). In one certain example of the invention, the HAH compound is 2,3,7,8-TCDD.

In addition, the host cell as used in the invention is particularly a hepatoma cell line, and more particularly is a commercially available cell line selected from the group consisting of H4-II-E, Hepa-1c1c7, Hepa 1-6, BNL CL.2, Clone 9, and BNL 1NG A.2.

A "sample" as used herein may be from food (e.g. milk or fish), biopsy (e.g. blood) or environmental water (e.g. river water).

In addition, the introduction of the recombinant construct into the host cell according to the invention can be effected in principle by all methods with which the skilled persons is familiar. Methods for introducing nucleic acids into host cells such as calcium chloride treatment, electroporation, DEAE-dextrin-mediated transfection, lipofection and microinjection are well known in the art. In a certain example of the invention, the introduction of the recombinant construct into the host cell is conducted by transient transfection. "Transient transfection" as used herein refers to a type of transfection in which the exogenous DNA is not stably incorporated into the recipient host cell's chromosomal DNA and functions for only a limited time. Transiently transfected DNA is generally located predominantly within a cell's cytoplasm.

Further, detection of the expression of the reporter gene can be accomplished through various methods known in this art, including, but are not limited to colorimetric, fluorimetric or luminometric assays depending on the natural of the reporter gene as used. In a certain example, the reporter gene as used in the present invention is luciferase and therefore a luminometric assay is conducted for detection of the expression of the reporter gene. Details for conducting the method of the invention are described in the examples below.

The present invention will now be described more specifically with reference to the following embodiments, which are provided for the purpose of demonstration rather than limitation.

Example 1

Figure 3:
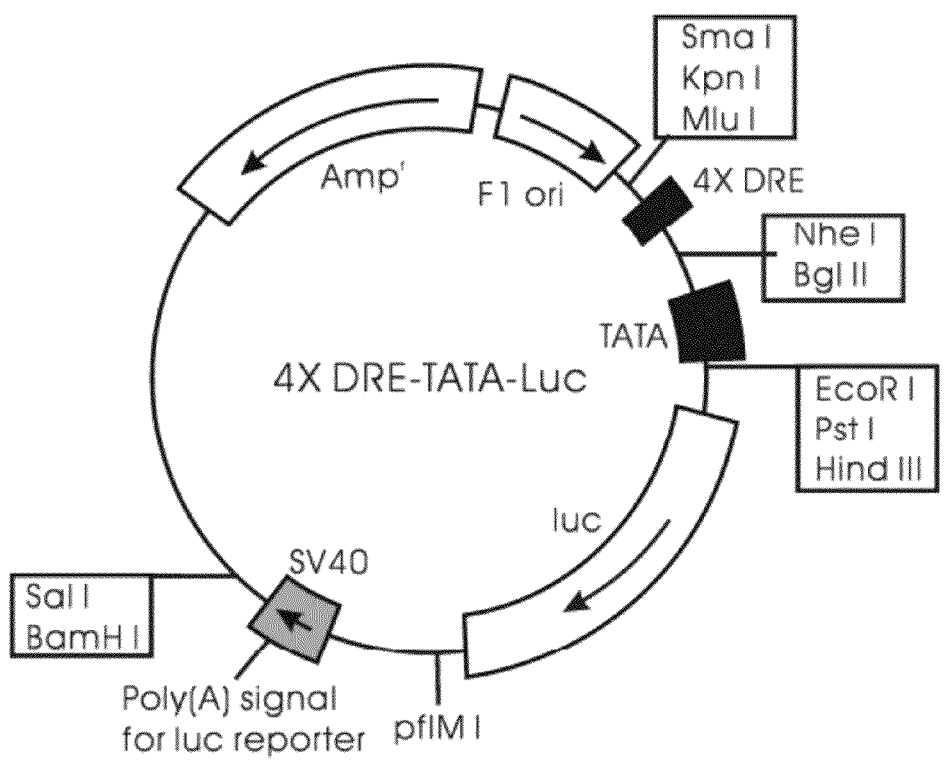
FIG. 3 shows the map of 4XDRE-TATA-Luc plasmid as described in Example 1.

Generation of Recombinant Adenovirus Construct of the Invention 1.1 4XDRE-TATA-Luc Plasmid 4XDRE-TATA-Luc plasmid was constructed by cloning four copies of DREs of human CYP1A1 in front of a TATA box and a firefly luciferase gene. Briefly, the pGL2 plasmid (Promega, USA) was digested with BglII and HindIII to remove the SV 40 promoter and then ligated with a TATA box, resulting in a TATA Luc vector (FIG. 1). Four single-stranded DNA molecules of SEQ ID NOS: 4 to 7, respectively, as shown in FIG. 2, were designed and synthesized and subjected to annealing reactions. Particularly, the single-stranded DNA molecules of SEQ ID NOS: 4 and 5 annealed together to make a first double stranded segment, and the single-stranded DNA molecules of SEQ ID NOS: 6 and 7 annealed together to make a second double stranded segment; these two double stranded segments were sequentially ligated into the above-mentioned TATA Luc vector, resulting in the 4XDRE-TATA-Luc plasmid (5686 bp). See FIG. 3

1.2 pAdTrack-4XDRE-TATA-Luc Plasmid

Figure 4:
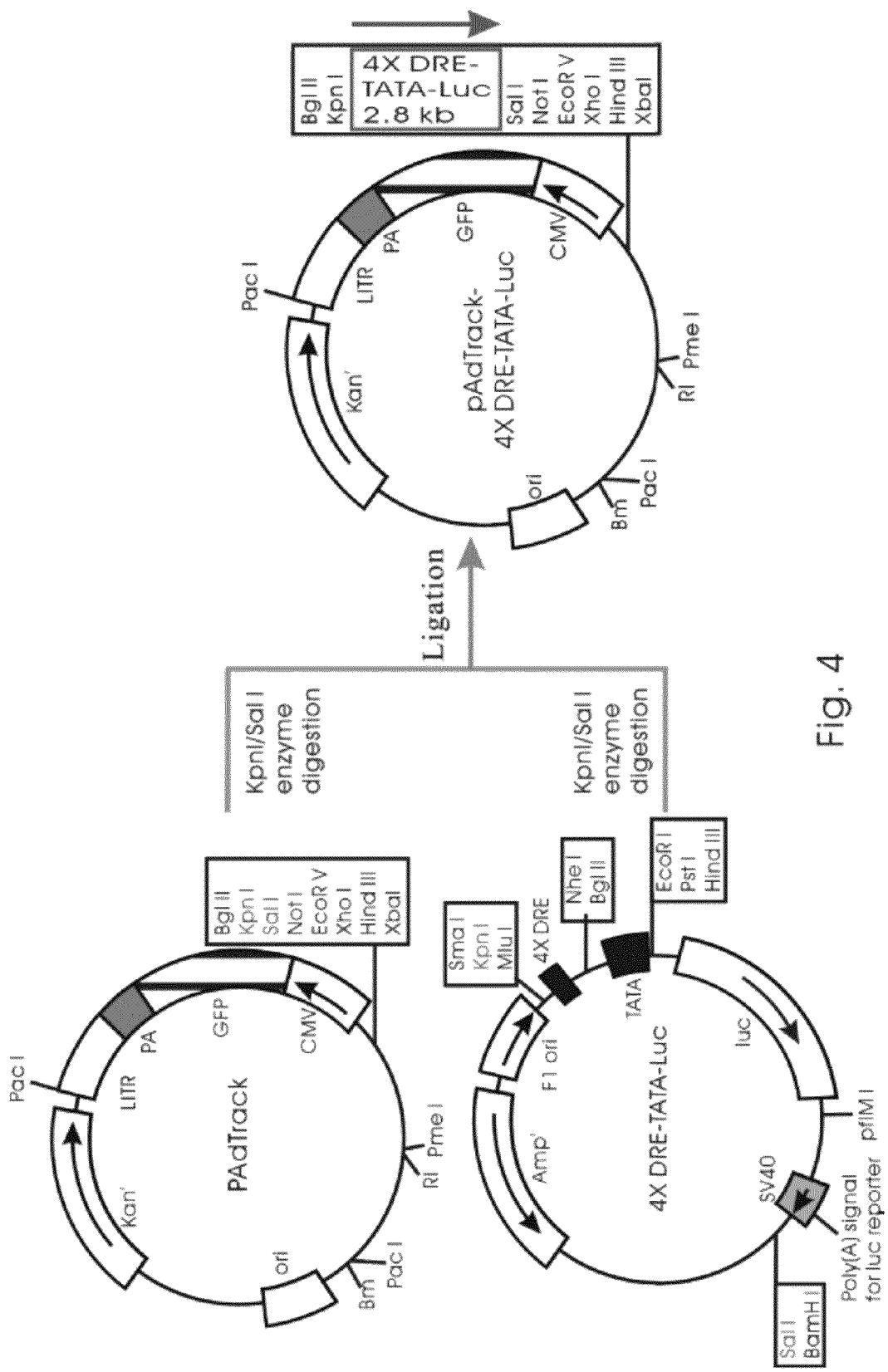
FIG. 4 shows the construction and map of pAdTrack-4XDRE-TATA-Luc as described in Example 1.

Subsequently, the 4XDRE-TATA-Luc plasmid was digested with KpnI and SalI to obtain the 4XDRE-TATA-luciferase fragment (2831 bp), which was then ligated into KpnI/SalI-digested pAdTrack (8.3 kb, Stratagene, Calif.), resulting a pAdTrack-4XDRE-TATA-Luc plasmid (11.1 kb). FIG. 4 shows the construction and map of pAdTrack-4XDRE-TATA-Luc.

1.3 AdEasy-4XDRE-TATA-Luc

Figure 5:
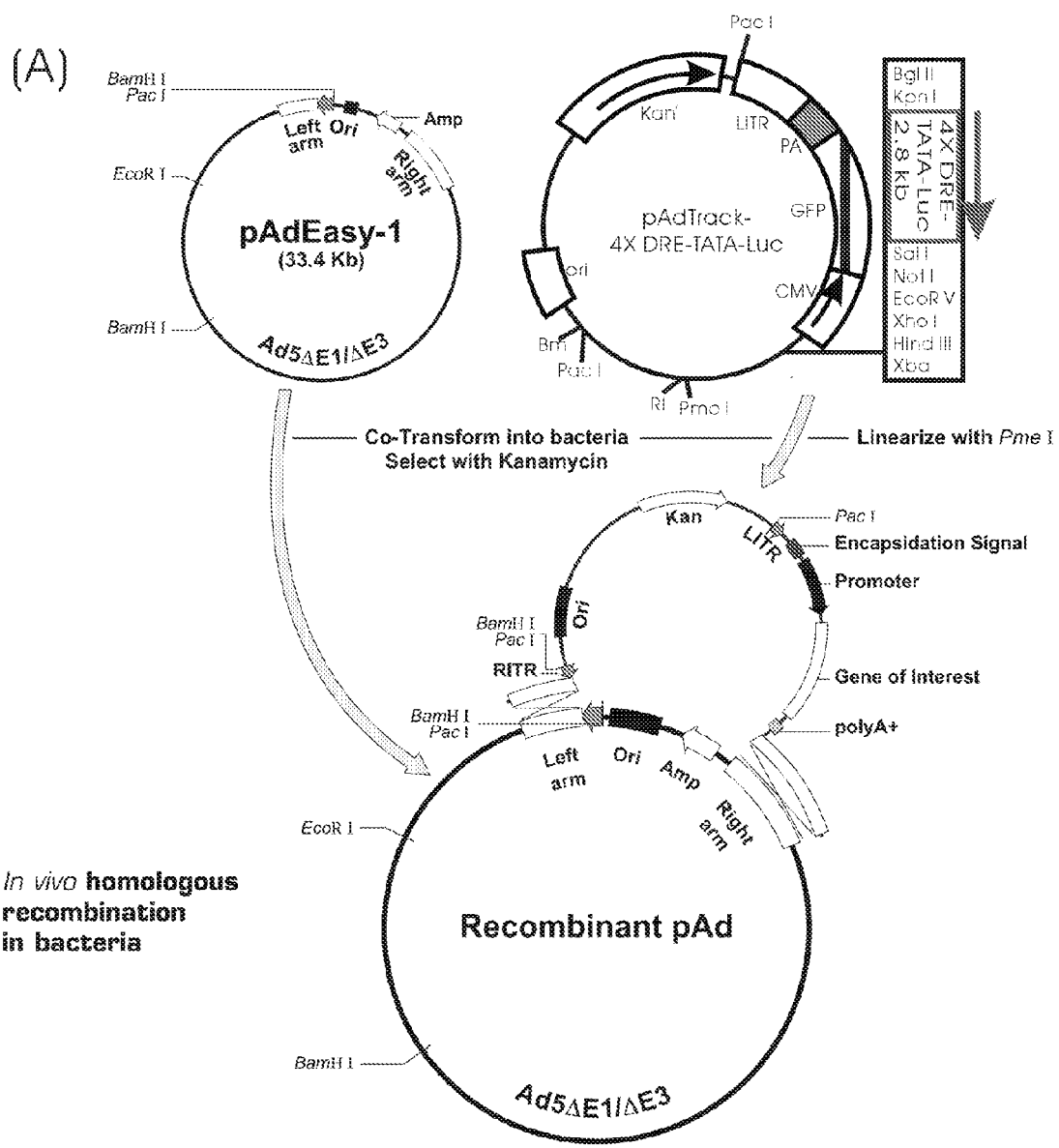
FIG. 5 shows (A) the construction of AdEasy-4XDRE-TATA-Luc as described in Example 1 wherein the double underlined segments indicate DREs, (B) the nucleotide sequence of SEQ ID NO: 1 covering the four copies of DREs (double underlined) in AdEasy-4XDRE-TATA-Luc, (C) the nucleotide sequence of SEQ ID NO: 2 covering the four copies of DREs (double underlined) together with a TATA box in AdEasy-4XDRE-TATA-Luc, and (D) the nucleotide sequence of SEQ ID NO: 3 covering the four copies of DREs (double underlined) extending to the TATA box and the subsequent luciferase coding sequence (underlined with dashed lines) as well as the poly A sequence (underlined with curved lines) in AdEasy-4XDRE-TATA-Luc. The arrows indicate the 5' to 3' direction of the DRE consensus sequence i.e. 5'-TNGCGTG-3' where N means any nucleotide of A, T, G and C.

The pAdTrack-4XDRE-TATA-Luc plasmid was digested with Pme I and purified. The purified Pme I-digested pAdTrack-4XDRE-TATA-Luc was then co-transformed with pAdEasy-1 (Stratagene, Calif.) into $E.\ coli$ BJ5183 for in vivo homologous recombination, resulting in the recombinant adenovirus construct of the invention, namely AdEasy-4XDRE-TATA-Luc. FIG. 5(A) shows the construction of the AdEasy-4XDRE-TATA-Luc plasmid. A DNA sequencing analysis was then conducted to confirm the nucleotide sequences of AdEasy-4XDRE-TATA-Luc. FIG. 5(B) shows the sequence of SEQ ID NO: 1 covering the four copies of DREs in AdEasy-4XDRE-TATA-Luc, (C) shows the nucleotide sequence of SEQ ID NO: 2 covering the four copies of DREs together with a TATA box in AdEasy-4XDRE-TATA-Luc, and (D) shows the nucleotide sequence of SEQ ID NO: 3 covering the four copies of DREs extending to the TATA box and the subsequent luciferase coding sequence as well as the poly A sequence in AdEasy-4XDRE-TATA-Luc.

The recombinant adenovirus construct was further purified and concentrated as described previously (Kanegae et al., 1994), and kept at −20° C. before use. For long term storage, it is suggested to keep the construct at −80° C.

Example 2

Adenoviral Infection and Luciferase Activity Measurements

Figure 6:
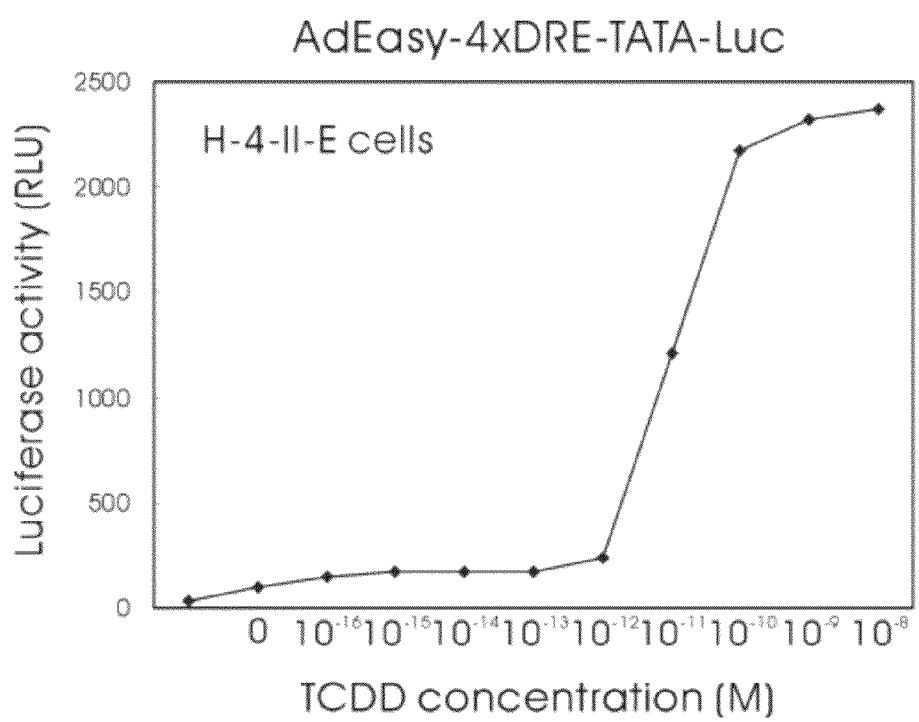
FIG. 6 shows the result of the luciferase assay as conducted in Example 1.
Figure 5:
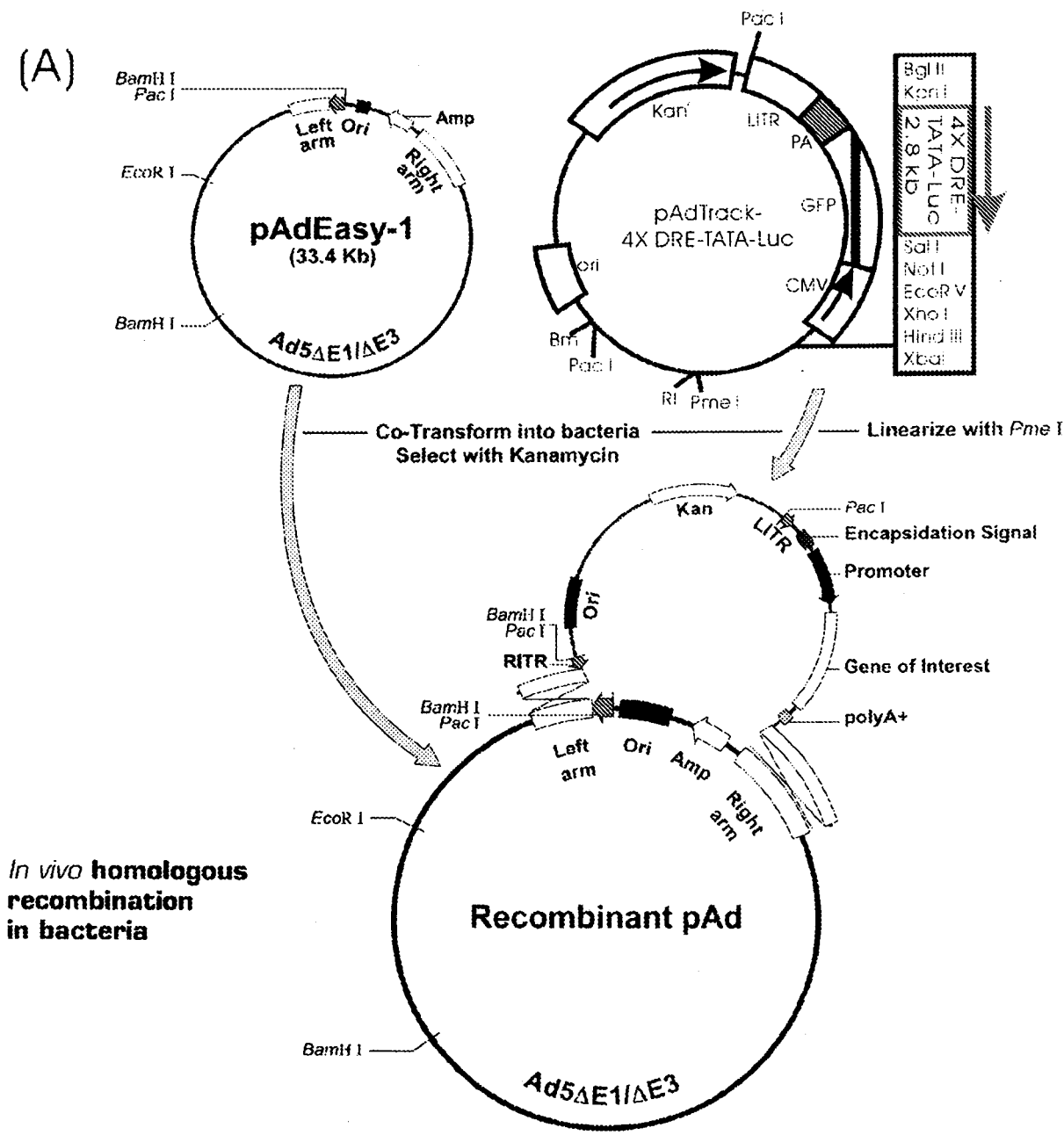
Figure 6:
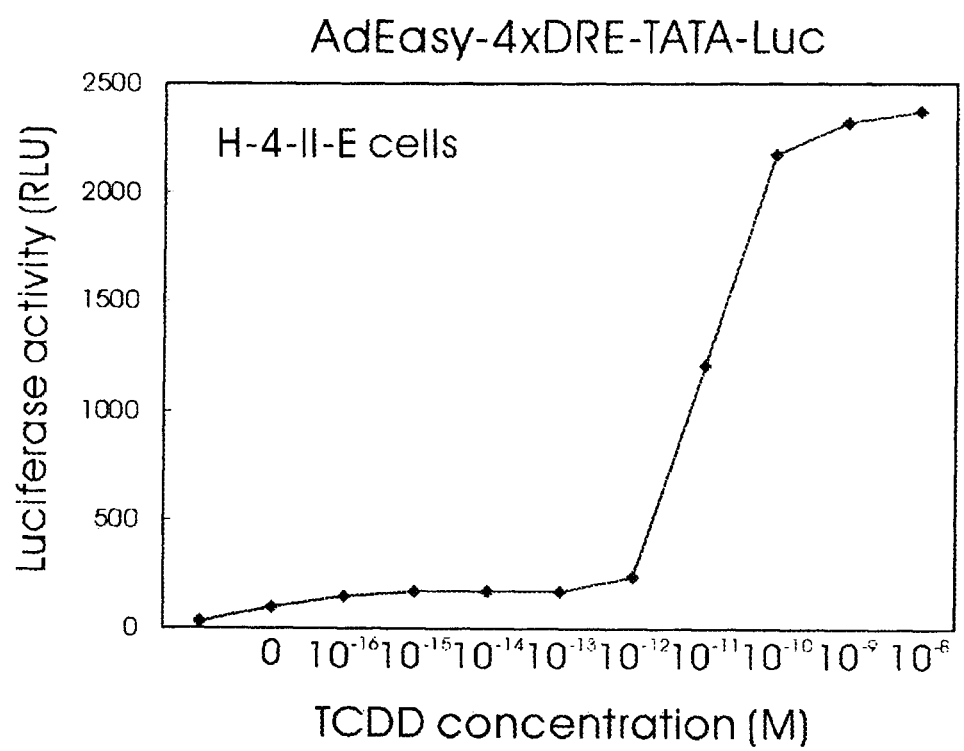

H-4-II-E cells (Bioresources Collection and Research Center (BCRC), Food Industry Research and Development Institute (FIRDI), Hsinchu, Taiwan) were seeded on 96-well plates at a density of 2×10⁴ cells/well in culture medium (80% Minimum essential medium Eagle with 0.1 mM non-essential amino acids, Earle's BSS, 10% fetal bovine serum and 10% calf serum) and cultured overnight in a humidified atmosphere containing 5% CO2 at 37° C. Subsequently, the cells were incubated with AdEasy-4XDRE-TATA-Luc as obtained in Example 1 at a multiplicity of infection (MOI) of one particles/cell for 16 hours. The infected cells were then treated with different concentrations of TCDD (Supelco, Bellefonte, Pa., USA) for 24 hours. TCDD stocks were prepared in DMSO. The final DMSO concentration in culture medium is 0.1%. Luciferase activity was measured by Luciferase Assay System (Promega, Madison, Wis., USA) according to the standard protocol as provided using the programmed microplate luminometer MicroLumatPlus LB96V (EG&G Berthold, Germany). The luciferase activity was expressed as relative light units (RLU). FIG. 6 shows the results of the luciferase activity as measured.

As shown in FIG. 6, the recombinant adenovirus construct of the invention has revealed a detection limit being around $10^{-12}$ M and particularly shown a steep slope between the concentrations of $10^{-12}$ to $10^{-10}$ M, indicating that a strong signal can be detected once the amount of TCDD is over the limit, and therefore the recombinant adenovirus construct of the invention is very effective in a preliminary test to determine the presence or absence of dioxins in a sample.

AdEasy-4XDRE-TATA-Luc were also introduced into other cells, including Hepa-1c1c7 (BCRC, FIRDI, Hsinchu, Taiwan), heap 1-6 (BCRC, FIRDI, Hsinchu, Taiwan), BNL CL.2 (BCRC, FIRDI, Hsinchu, Taiwan), Clone 9 (BCRC, FIRDI, Hsinchu, Taiwan), and BNL 1NG A.2 (BCRC, FIRDI, Hsinchu, Taiwan), and demonstrated to exhibit similar detection curves as in FIG. 6 (data not shown).

We claim:

1. A recombinant construct for detection of a halogenated aromatic hydrocarbon compound, comprising a reporter gene which is operatively linked to a regulatory sequence including the nucleotide sequence of SEQ ID NO: 1 and a promoter.

2. The recombinant construct of claim 1, which is an adenoviral construct.

3. The recombinant construct of claim 2, which is a serotype 5 adenovirus (Ad5) adenoviral construct.

4. The recombinant construct of claim 1, wherein the promoter includes a TATA box.

5. The recombinant construct of claim 1, wherein the reporter gene encodes a bioluminescent reporter protein.

6. The recombinant construct of claim 5, wherein the reporter protein is luciferase.

7. The recombinant construct of claim 4, wherein the regulatory sequence includes the nucleotide sequence of SEQ ID NO: 2.

8. The recombinant construct of claim 1, comprising the nucleotide sequence of SEQ ID NO: 3.

9. A method for determining if a halogenated aromatic hydrocarbon (HAH) compound is present in a sample comprising:

(a) introducing the recombinant construct of claim 1 into a host cell that expresses an aryl hydrocarbon receptor (AhR);

(b) incubating the host cell with the sample; and (c) detecting the expression of the reporter gene as indicator for the presence of the HAH compounds in the sample.

10. The method of claim 9, wherein the HAH compound is capable of binding to the AhR.

11. The method of claim 9, wherein the HAH compound is selected from the group consisting of polychlorinated dibenzo-p-dioxins (PCDDs), polychlorinated dibenzofurans (PCDFs), polychlorinated biphenyls (PCBs) and combinations thereof.

12. The method of claim 9, wherein the HAH compound is 2,3,7,8-tetrachlorodibenzo-p-dioxin (2,3,7,8-TCDD).

13. The method of claim 9, wherein the recombinant construct is an adenoviral construct.

14. The method of claim 13, wherein the adenoviral construct is an Ad5 construct.

15. The method of claim 9, wherein the promoter includes a TATA box.

16. The method of claim 9, wherein the reporter gene encodes luciferase.

17. The method of claim 9, wherein the regulatory sequence includes the nucleotide sequence of SEQ ID NO: 2.

18. The method of claim 9, wherein the recombinant construct comprises the nucleotide sequence of SEQ ID NO: 3.

19. The method of claim 9, wherein the host cell is a hepatoma cell line.

20. The method of claim 19, wherein the hepatoma cell line is selected from the group consisting of H4-II-E, Hepa-1c1c7, Hepa 1-6, BNL CL.2, Clone 9, and BNL 1NG A.2.

\* \* \* \* \*

UNITED STATES PATENT AND TRADEMARK OFFICE
CERTIFICATE OF CORRECTION

PATENT NO. : 8,247,224 B2
APPLICATION NO. : 12/726099
DATED : August 21, 2012
INVENTOR(S) : Tsui-Chun Tsou et al.

It is certified that error appears in the above-identified patent and that said Letters Patent is hereby corrected as shown below:

Delete drawing sheets 5-9 and substitute the attached drawing sheets 5-9 therefor.

Signed and Sealed this
Eighteenth Day of December, 2012

David J. Kappos
*Director of the United States Patent and Trademark Office*

(B)

CCC<u>TCGCGT</u>GACTGCGAGGTCCTTCT<u>CACGCA</u>ACGCCTGA<u>CGCGT</u>CGCCG
    DRE→                      ←DRE

GCG<u>CACGCAA</u>GCTAGCAGCGCTTCT<u>CACGCGA</u>GCCGGG
   ←DRE                   ←DRE (C)

CCCGGGAG<u>GTAC</u>CCCC<u>TCGCGT</u>GACTGCGAGGTCCTTCT<u>CACGCA</u>ACGCCTGA<u>CGCGT</u>CGCCGGCG<u>CAC</u>
       KpnI     DRE→                 ←DRE     MluI        ←DRE

<u>GCAA</u>GCTAGCAGCGCTTCT<u>CACGCGA</u>GCCGGG<u>AGATCT</u>AGAGGG<u>TATATAAT</u>GGAATTCCTGCAG<u>AAGC</u>
            ←DRE        BglII     TATA                HindIII
                                           box
<u>TT</u>

Fig. 5 (continued)

(D)

CCCGGGAGGTACCCCCTCCCGTGACTGCGAGGTCCTTCTCACGCAACGCCTGACGCGTCGCCGGCGCAC
CCAAGCTAGCAGCGCTTCTCACGCGAGCCGGGAGATCTAGAGGGTATATAATGGAATTCCTGCAGAAGC
TTGGCATTCCGGTACTGTTGGTAAAATGGAAGACGCCAAAAACATAAAGAAAGGCCCGGCGCCATTCTA
TCCTCTAGAGGATGGAACCGCTGGAGAGCAACTGCATAAGGCTATGAAGAGATACGCCCTGGTTCCTGG
AACAATTGCTTTTACAGATGCACATATCGAGGTGAACATCACGTACGCGGAATACTTCGAAATGTCCGT
TCGGTTGGCAGAAGCTATGAAACGATATGGGCTGAATACAAATCACAGAATCGTCGTATGCAGTGAAAA
CTCTCTTCAATTCTTTATGCCGGTGTTGGGCGCGTTATTTATCGGAGTTGCAGTTGCGCCCGCGAACGA
CATTTATAATGAACGTGAATTGCTCAACAGTATGAACATTTCGCAGCCTACCGTAGTGTTTGTTTCCAA
AAAGGGGTTGCAAAAAATTTTGAACGTGCAAAAAAAATTACCAATAATCCAGAAAATTATTATCATGGA
TTCTAAAACGGATTACCAGGGATTTCAGTCGATGTACACGTTCGTCACATCTCATCTACCTCCCGGTTT
TAATGAATACGATTTTGTACCAGAGTCCTTTGATCGTGACAAAACAATTGCACTGATAATGAATTCCTC
TGGATCTACTGGGTTACCTAAGGGTGTGGCCCTTCCGCATAGAACTGCCTGCGTCAGATTCTCGCATGC
CAGAGATCCTATTTTTGGCAATCAAATCATTCCGGATACTGCGATTTTAAGTGTTGTTCCATTCCATCA
CGGTTTTGGAATGTTTACTACACTCGGATATTTGATATGTGGATTTCGAGTCGTCTTAATGTATAGATT
TGAAGAAGAGCTGTTTTTACGATCCCTTCAGGATTACAAAATTCAAAGTGCGTTGCTAGTACCAACCCT
ATTTTCATTCTTCGCCAAAAGCACTCTGATTGACAAATACGATTTATCTAATTTACACGAAATTGCTTC
TGGGGGCGCACCTCTTTCGAAAGAAGTCGGGGAAGCGGTTGCAAAACGCTTCCATCTTCCAGGGATACG
ACAAGGATATGGGCTCACTGAGACTACATCAGCTATTCTGATTACACCCGAGGGGGATGATAAACCGGG
CGCGGTCGGTAAAGTTGTTCCATTTTTTGAAGCGAAGGTTGTGGATCTGGATACCGGGAAAACGCTGGG
CGTTAATCAGAGAGGCGAATTATGTGTCAGAGGACCTATGATTATGTCCGGTTATGTAAACAATCCGGA
AGCGACCAACGCCTTGATTGACAAGGATGGATGGCTACATTCTGGAGACATAGCTTACTGGGACGAAGA
CGAACACTTCTTCATAGTTGACCGCTTGAAGTCTTTAATTAAATACAAAGGATATCAGGTGGCCCCCGC
TGAATTGGAATCGATATTGTTACAACACCCCAACATCTTCGACGCGGGCGTGGCAGGTCTTCCCGACGA
TGACGCCGGTGAACTTCCCGCCGCCGTTGTTGTTTTGGAGCACGGAAAGACGATGACGGAAAAAGAGAT
CGTGGATTACGTCGCCAGTCAAGTAACAACCGCGAAAAAGTTGCGCGGAGGAGTTGTGTTTGTGGACGA
AGTACCGAAAGGTCTTACCGGAAAACTCGACGCAAGAAAAATCAGAGAGATCCTCATAAAGGCCAAGAA
GGGCGGAAAGTCCAAATTGTAAAATGTAACTGTATTCAGCGATGACGAAATTCTTAGCTATTGTAATAC

TGCGATGAGTGGCAGGGCGGGGCGTAATTTTTTTAAGGCAGTTATTGGTGCCCTTAAACGCCTGGTTGC

TACGCCTGAATAAGTGATAATAAGCGGATGAATGGCAGAAATTCGCCGGATCTTTGTGAAGGAACCTTA

CTTCTGTGGTGTGACATAATTGGACAAACTACCTACAGAGATTTAAAGCTCTAAGGTAAATATAAAATT

TTTAAGTGTATAATGTGTTAAACTACTGATTCTAATTGTTTGTGTATTTTAGATTCCAACCTATGGAAC

TGATGAATGGGAGCAGTGGTGGAATGCCTTTAATGAGGAAAACCTGTTTTGCTCAGAAGAAATGCCATC

TAGTGATGATGAGGCTACTGCTGACTCTCAACATTCTACTCCTCCAAAAAAGAAGAGAAAGGTAGAAGA

CCCCAAGGACTTTCCTTCAGAATTGCTAAGTTTTTTGAGTCATGCTGTGTTTAGTAATAGAACTCTTGC

TTGCTTTGCTATTTACACCACAAAGGAAAAAGCTGCACTGCTATACAAGAAAATTATGGAAAAATATTC

TGTAACCTTTATAAGTAGGCATAACAGTTATAATCATAACATACTGTTTTTTCTTACTCCACACAGGCA

TAGAGTGTCTGCTATTAATAACTATGCTCAAAAATTGTGTACCTTTAGCTTTTTAATTTGTAAAGGGGT

TAATAAGGAATATTTGATGTATAGTGCCTTGACTAGAGATCATAATCAGCCATACCACATTTGTAGAGG

TTTTACTTGCTTTAAAAAAACCTCCCACACCTCCCCCTGAACCTGAAACATAAAATGAATGCAATTGTTG

TTGTTAACTTGTTTATTGCAGCTTATAATGGTTACAAATAAAGCAATAGCATCACAAATTTCACAAATA

AAGCATTTTTTTCACTGCATTCTAGTTGTGGTTTGTCCAAACTCATCAATGTATCTTATGATGTCTGGA

TCCGTCGACCGATGCCCTTGAGAGCCTTCAACCCAGTCAGCTCCTTCCGGTGGGCGCGGGGCATGACTA
   Sal I

Fig. 5 (continued)

SEQUENCE LISTING

```
<160> NUMBER OF SEQ ID NOS: 7

<210> SEQ ID NO 1
<211> LENGTH: 88
<212> TYPE: DNA
<213> ORGANISM: Artificial Sequence
<220> FEATURE:
<223> OTHER INFORMATION: construct nucleotide sequences

<400> SEQUENCE: 1
ccctcgcgtg actgcgaggt ccttctcacg caacgcctga cgcgtcgccg gcgcacgcaa      60
gctagcagcg cttctcacgc gagccggg                                         88

<210> SEQ ID NO 2
<211> LENGTH: 140
<212> TYPE: DNA
<213> ORGANISM: Artificial Sequence
<220> FEATURE:
<223> OTHER INFORMATION: construct nucleotide sequences

<400> SEQUENCE: 2
cccgggaggt accccctcgc gtgactgcga ggtccttctc acgcaacgcc tgacgcgtcg      60
ccggcgcacg caagctagca gcgcttctca cgcgagccgg gagatctaga gggtatataa     120
tggaattcct gcagaagctt                                                 140

<210> SEQ ID NO 3
<211> LENGTH: 2898
<212> TYPE: DNA
<213> ORGANISM: Artificial Sequence
<220> FEATURE:
<223> OTHER INFORMATION: construct nucleotide sequences

<400> SEQUENCE: 3
cccgggaggt accccctcgc gtgactgcga ggtccttctc acgcaacgcc tgacgcgtcg      60
ccggcgcacg caagctagca gcgcttctca cgcgagccgg gagatctaga gggtatataa     120
tggaattcct gcagaagctt ggcattccgg tactgttggt aaaatggaag acgccaaaaa     180
cataaagaaa ggcccggcgc cattctatcc tctagaggat ggaaccgctg gagagcaact     240
gcataaggct atgaagagat acgccctggt tcctggaaca attgcttttα cagatgcaca     300 tatcgaggtg aacatcacgt acgcggaata cttcgaaatg tccgttcggt tggcagaagc     360
tatgaaacga tatgggctga atacaaatca cagaatcgtc gtatgcagtg aaaactctct     420
```

```
tcaattctttt atgccggtgt tgggcgcgtt atttatcgga gttgcagttg cgcccgcgaa    480
cgacatttat aatgaacgtg aattgctcaa cagtatgaac atttcgcagc ctaccgtagt    540
gtttgtttcc aaaaagggt tgcaaaaaat tttgaacgtg caaaaaaaat taccaataat    600
ccagaaaatt attatcatgg attctaaaac ggattaccag ggatttcagt cgatgtacac    660
gttcgtcaca tctcatctac ctcccggttt taatgaatac gattttgtac cagagtcctt    720
tgatcgtgac aaaacaattg cactgataat gaattcctct ggatctactg ggttacctaa    780
gggtgtggcc cttccgcata gaactgcctg cgtcagattc tcgcatgcca gagatcctat    840
ttttggcaat caaatcattc cggatactgc gattttaagt gttgttccat tccatcacgg    900
ttttggaatg tttactacac tcggatattt gatatgtgga tttcgagtcg tcttaatgta    960
tagatttgaa gaagagctgt ttttacgatc ccttcaggat tacaaaattc aaagtgcgtt   1020
gctagtacca accctatttt cattcttcgc caaaagcact ctgattgaca aatacgattt   1080
atctaattta cacgaaattg cttctggggg cgcacctctt tcgaaagaag tcggggaagc   1140
ggttgcaaaa cgcttccatc ttccagggat acgacaagga tatgggctca ctgagactac   1200
atcagctatt ctgattacac ccgaggggga tgataaaccg ggcgcggtcg gtaaagttgt   1260
tccatttttt gaagcgaagg ttgtggatct ggataccggg aaaacgctgg gcgttaatca   1320
gagaggcgaa ttatgtgtca gaggacctat gattatgtcc ggttatgtaa caatccgga   1380 agcgaccaac gccttgattg acaaggatgg atggctacat tctggagaca tagcttactg   1440
ggacgaagac gaaacacttct tcatagttga ccgcttgaag tctttaatta aatacaaagg   1500
atatcaggtg gcccccgctg aattggaatc gatattgtta caacacccca acatcttcga   1560
cgcgggcgtg gcaggtcttc ccgacgatga cgccggtgaa cttcccgccg ccgttgttgt   1620
tttggagcac ggaaagacga tgacggaaaa agagatcgtg gattacgtcg ccagtcaagt   1680
aacaaccgcg aaaagttgc gcggaggagt tgtgtttgtg gacgaagtac cgaaaggtct   1740
taccggaaaa ctcgacgcaa gaaaaatcag agagatcctc ataaaggcca agaagggcgg   1800
aaagtccaaa ttgtaaaatg taactgtatt cagcgatgac gaaattctta gctattgtaa   1860
tactgcgatg agtggcaggg cggggcgtaa ttttttttaag gcagttattg gtgcccttaa   1920
acgcctggtt gctacgcctg aataagtgat aataagcgga tgaatggcag aaattcgccg   1980
gatctttgtg aaggaacctt acttctgtgg tgtgacataa ttggacaaac tacctacaga   2040
gatttaaagc tctaaggtaa atataaaatt tttaagtgta taatgtgtta aactactgat   2100
tctaattgtt tgtgtatttt agattccaac ctatggaact gatgaatggg agcagtggtg   2160
gaatgccttt aatgaggaaa acctgttttg ctcagaagaa atgccatcta gtgatgatga   2220
ggctactgct gactctcaac attctactcc tccaaaaaag aagagaaagg tagaagaccc   2280
caaggacttt ccttcagaat tgctaagttt tttgagtcat gctgtgttta gtaatagaac   2340
tcttgcttgc tttgctattt acaccacaaa ggaaaaagct gcactgctat acaagaaaat   2400
tatggaaaaa tattctgtaa cctttataag taggcataac agttataatc ataacatact   2460
gttttttctt actccacaca ggcatagagt gtctgctatt aataactatg ctcaaaaatt   2520
gtgtaccttt agcttttaa tttgtaaagg ggttaataag gaatatttga tgtatagtgc   2580
cttgactaga gatcataatc agccatacca catttgtaga ggttttactt gctttaaaaa   2640
acctcccaca cctcccccctg aacctgaaac ataaaatgaa tgcaattgtt gttgttaact   2700
tgtttattgc agcttataat ggttacaaat aaagcaatag catcacaaat ttcacaaata   2760
aagcattttt ttcactgcat tctagttgtg gtttgtccaa actcatcaat gtatcttatg   2820
```

-continued

```
atgtctggat ccgtcgaccg atgcccttga gagccttcaa cccagtcagc tccttccggt    2880
gggcgcgggg catgacta                                                  2898
```

```
<210> SEQ ID NO 4
<211> LENGTH: 49
<212> TYPE: DNA
<213> ORGANISM: Artificial Sequence
<220> FEATURE:
<223> OTHER INFORMATION: first single strnaded DNA

<400> SEQUENCE: 4
cgcgtcgccg gcgcacgcaa gctagcagcg cttctcacgc gagccggga                 49

<210> SEQ ID NO 5
<211> LENGTH: 49
<212> TYPE: DNA
<213> ORGANISM: Artificial Sequence
<220> FEATURE:
<223> OTHER INFORMATION: second single stranded DNA

<400> SEQUENCE: 5
gatctcccgg ctcgcgtgag aagcgctgct agcttgcgtg cgccggcga                 49

<210> SEQ ID NO 6
<211> LENGTH: 41
<212> TYPE: DNA
<213> ORGANISM: Artificial Sequence
<220> FEATURE:
<223> OTHER INFORMATION: third single stranded DNA

<400> SEQUENCE: 6
cccctcgcgt gactgcgagg tccttctcac gcaacgcctg a                         41

<210> SEQ ID NO 7
<211> LENGTH: 49
<212> TYPE: DNA
<213> ORGANISM: Artificial Sequence
<220> FEATURE:
<223> OTHER INFORMATION: forth single stranded DNA

<400> SEQUENCE: 7
cgcgtcaggc gttgcgtgag aaggacctcg cagtcacgcg aggggtac                  49
```